United States Patent
Giselbrecht et al.

(10) Patent No.: US 6,258,572 B1
(45) Date of Patent: Jul. 10, 2001

(54) PROCESS FOR PREPARING L-ASPARTIC ACID

(75) Inventors: Karl-Heinz Giselbrecht, Pasching; Josef Schaller, Linz, both of (AT)

(73) Assignee: DSM Fine Chemicals Austria Nfg GmbH & CoKG, Linz (AT)

( * ) Notice: Subject to any disclaimer, the term of this patent is extended or adjusted under 35 U.S.C. 154(b) by 0 days.

(21) Appl. No.: 09/315,044

(22) Filed: May 20, 1999

(30) Foreign Application Priority Data

May 22, 1998 (AT) .................................................. 878/98

(51) Int. Cl.$^7$ ................................................... C12P 13/20
(52) U.S. Cl. ........................................... 435/109; 435/232
(58) Field of Search ..................................... 435/109, 232

(56) References Cited

U.S. PATENT DOCUMENTS 5,952,206 * 9/1999 Giselbrecht et al. ................. 435/109
6,150,142 * 11/2000 Mukouyama et al. ................ 435/109

FOREIGN PATENT DOCUMENTS 298438   5/1972 (AT) .
0 798 377  10/1997 (EP) .

OTHER PUBLICATIONS

*Chemical Abstracts*, 238:74403s (1998).

* cited by examiner

*Primary Examiner*—Herbert J. Lilling
(74) *Attorney, Agent, or Firm*—Wenderoth, Lind & Ponack, L.L.P.

(57) ABSTRACT

An improved process for preparing L-aspartic acid by enzyme-catalyzed reaction of fumaric acid with ammonia, in which process L-aspartic acid is precipitated out by nitric acid and the resultant mother liquor is subjected to a nanofiltration.

9 Claims, 1 Drawing Sheet

PROCESS FOR PREPARING L-ASPARTIC ACID

Figure 1:
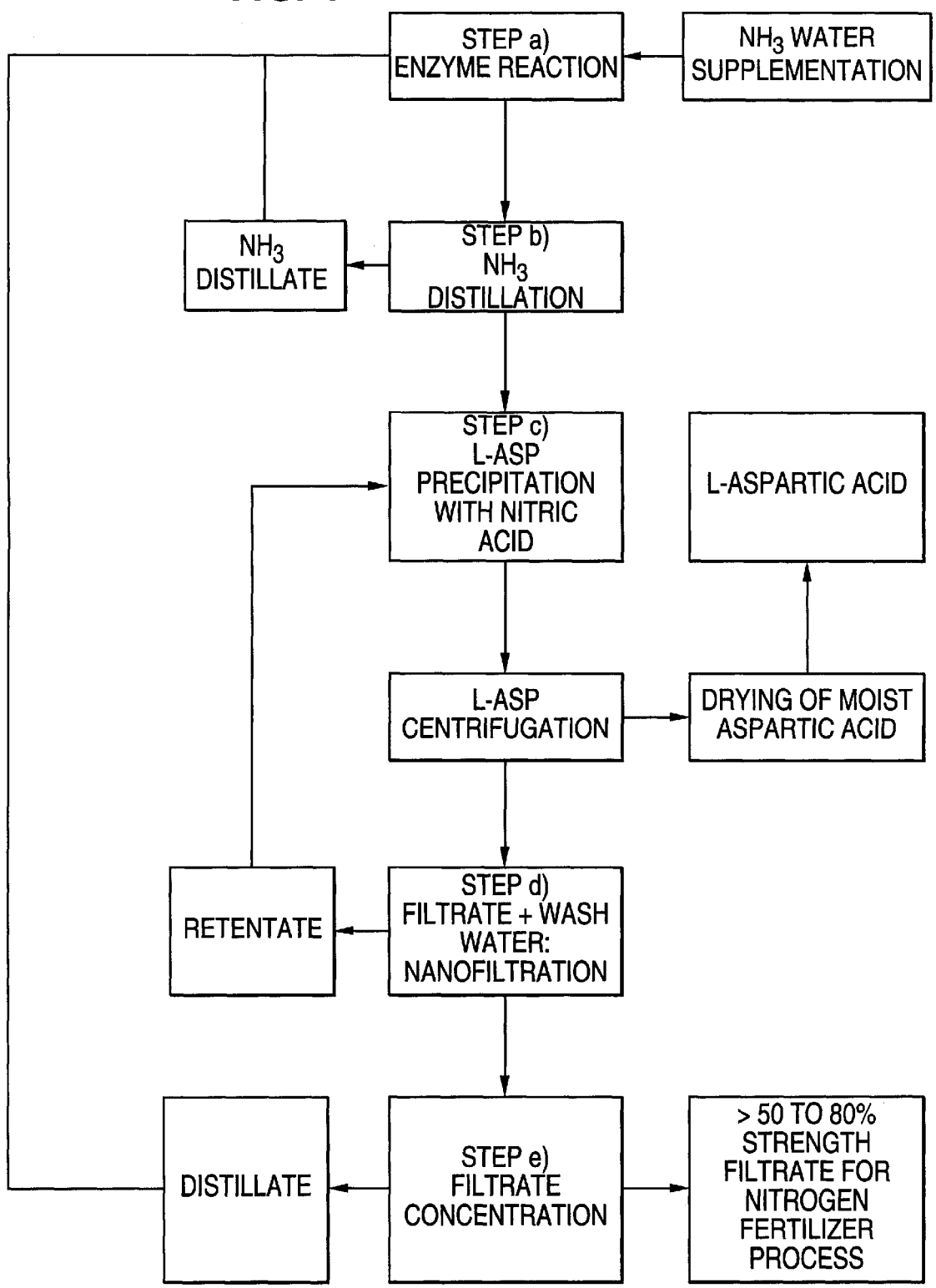

L-Aspartic acid is an essential starting material for a wide variety of additives for the pharmaceutical industry and the food sector. For example, L-aspartic acid is used for preparing artificial sweetener, such as aspartame. Therefore, a multiplicity of chemical and enzymatic processes have already been described for preparing L-aspartic acid. In the enzymatic variants, L-aspartic acid is usually obtained by enzymatic addition of ammonia to fumaric acid with subsequent precipitation from the resultant ammonium L-aspartate solution.

According to the prior art, L-aspartic acid can be precipitated, for example, by adding sulfuric acid or hydrochloric acid or other acids, such as p-toluenesulfonic acid.

However, the disadvantages of this are that the loss of ammonia is high and a large amount of wastewater having a high concentration of ammonium salts of the acids used is discharged.

For this reason, attempts have been made to find possible methods of decreasing or completely avoiding the wastewater problem.

According to U.S. Pat. No. 4,560,653, the L-aspartic acid is precipitated, for example, by adding maleic acid. After separating off L-aspartic acid, the remaining mother liquor is subjected to an isomerization step in which maleic acid is isomerized into fumaric acid, for instance using a catalyst comprising bromine ions, then purified and fed back to the enzymatic reaction. In order to bypass the isomerization step, other suitable additives for precipitating L-aspartic acid have been sought.

In the Japanese Laid-Open Application JP 08-33493 (Chem. Abstracts 1224:315 167), the use of fumaric acid or salt of fumaric acid as precipitant is described. The disadvantage of this process variant is the poor water solubility of fumaric acid, as a result of which, during the workup of the mother liquor, either large amounts of water have to be distilled off or a very dilute procedure having high reaction volumes is necessary.

The object of the invention is therefore to find a process which avoids the previous problems in the precipitation of L-aspartic acid and leads to L-aspartic acid in high yields and high purity.

Unexpectedly, this object was achieved by using nitric acid as precipitant and subsequent nanofiltration of the mother liquor.

The invention therefore relates to an improved process for preparing L-aspartic acid by enzyme-catalyzed reaction of fumaric acid with ammonia, which comprises
a) reacting fumaric acid with ammonia to form ammonium L-aspartate in the presence of aspartase or aspartase-producing microorganisms in an inert diluent,
b) removing any excess ammonia from the reaction mixture and
c) precipitating L-aspartic acid by adding nitric acid, separating it off from the reaction mixture, washing and drying it, then
d) separating off residual L-aspartic acid and residual fumaric acid from the precipitation filtrate by nanofiltration, recycling the retentate to step c) and
e) concentrating the filtrate from step d), adding the resultant distillate in step a) to any ammonia excess separated off in step b) and feeding the concentrated filtrate to a nitrogen fertilizer process.

In the process according to the invention, L-aspartic acid is precipitated by nitric acid. The reaction streams are recirculated according to the invention. The process according to the invention can be seen in FIG. 1, where the reaction streams are shown diagrammatically.

The concentrated filtrate obtained in step e) can be introduced directly into the nitrogen fertilizer process.

The first step of the process according to the invention comprises the enzymatic reaction of fumaric acid with ammonia. The reaction takes place here in an inert diluent. Suitable inert diluents are water, water/ethanol or water/acetone mixtures and the like. Preferably, water is used. Fumaric acid can be used here in a concentration of up to the solubility limit, so that either a solution or a suspension is obtained. Into this solution or suspension is introduced ammonia, gaseous, liquefied or in the form of a from 10 to 35% strength by weight solution, as a result of which the temperature increases to 60° C. and a pH of between 7 and 9 is established.

Preferably, an aqueous 20 to 30% strength by weight ammonia solution is used. Into the resultant system, preferably a solution, is then stirred the 20 enzyme aspartase, or an aspartase-producing micro-organism, at from 20 to 60° C., preferably at from 30 to 50° C. In this addition of enzyme- or aspartase-producing microorganism, it is advantageous if the addition of ammonia gives a solution, since in the case of a suspension more enzyme is necessary, owing to adsorption of the enzyme and loss in activity caused by this. For a virtually quantitative reaction after up to from 24 to 30 hours, in this case, from 30 to 50 IU (enzyme activity) are required per mole of fumaric acid.

Aspartase-producing microorganisms are, for example, *Pseudomonas fluorescens, Protens vulgaris, Pseudomonas aeruginosa, Serratia marcescens, Bacterium succinium, Bacillus subtilis, Aerobacter aerogenes*, Micrococcus sp., *Escherichia coli*, inter alia.

Other suitable aspartase-producing microorganisms are described, for example, in U.S. Pat. No. 3,791,926 and U.S. Pat. No. 3,198,712.

In the process according to the invention, in addition, purified or synthetic aspartase can be used. The enzyme or the aspartase-producing microorganism can be added in liquid or immobilized form, as described, for example, in EP 0 127 940.

After completion of the reaction, the end of the reaction can be determined photometrically, for example, according to step b), if appropriate, the ammonia is separated off by distillation or stripping.

Step b) can be carried out at atmospheric pressure or under reduced pressure and at temperatures of from 30 to 110° C., preferably from 40 to 90° C.

Excess ammonia is removed from the reaction mixture in this case using familiar distillation methods, for example using short-path or thin-film evaporators, strippers etc. According to the distillation method, either, preferably, atmospheric pressure, or reduced pressure between 80 and 200 mbar is employed. The resultant ammonia distillate is reused as starting material for a subsequent further enzyme reaction a) together with the distillate from the subsequent process step d).

After the removal of ammonia, or directly after step a), the L-aspartic acid is precipitated as in step c) For this purpose, the ammonium L-aspartate solution is admixed with sufficient nitric acid to achieve a pH between 2 and 5, preferably up to the isoelectric point. Nitric acid is added in this case preferably as from 10 to 65% strength, particularly preferably as 60% strength, nitric acid. The temperature of the reaction mixture in this case is between 15 and 60° C., preferably between 20 and 35° C.

From the 2nd reaction cycle, in addition to the nitric acid, the retentate from the nanofiltration of the precipitation filtrate produced in the subsequent step d), which retentate comprises residual amounts of L-aspartic acid and fumaric acid, is added to the ammonium L-aspartate solution.

The reaction mixture is then cooled, preferably to 0 to −15° C. and the L-aspartic acid which has crystallized out is separated off, for example by filtration, such as by absorption filtration or by centrifugation. Preferably, L-aspartic acid is separated off by centrifugation or decanting.

The L-aspartic acid crystals filtered off are finally washed, preferably with water, and dried. The wash water can here be recycled to step a) or, preferably, subjected to the subsequent nanofiltration. The remaining precipitation filtrate produced after separating off L-aspartic acid, as well as the wash water are then subjected to a nanofiltration in step d). The pH in this case is preferably between 4 and 11, particularly preferably between 7 and 10, and is preferably set using $NH_3$. The pressure is preferably between 1 and 50 bar. The temperature is preferably 10 to 50° C., particularly preferably 15 to 30° C. Owing to the nanofiltration, the L-aspartic acid present in the filtrate, as well as residual amounts of fumaric acid as ammonium salts which are present in the retentate can be recovered from the filtrate. The resultant retentate is fed to the crystallization process in step c) from the 2nd reaction cycle.

The filtrate produced by the nanofiltration (approximately 20% strength ammonium nitrate solution) is concentrated in step e), for example by evaporation of water, until an over 50 to 80% strength, preferably an approximately 60 to 70% strength, ammonium nitrate solution is obtained. This solution can, as an ammonium nitrate solution free of organic carbon, be introduced into the nitrogen fertilizer process directly as material of value or starting material. The distillate remaining from the concentration is, from the 2nd cycle, together with any ammonia excess separated off in step b), added to the enzyme-catalyzed reaction in step a).

By means of the process according to the invention, L-aspartic acid can be obtained in quantitative yields, i.e. up to 99% and a content of >99.5%.

EXAMPLE 1

Into 850 ml (950 g) of L-aspartic acid reaction solution (DSM-Chemie Linz), comprising 240 g (1.8 mol) of L-aspartic acid, prepared by reaction from 210 g (1.8 mol) of fumaric acid, 200 ml of 25% strength by weight ammonia solution in 280 ml of $H_2O$, in the presence of 0.08 ml of aspartase solution (1100 IU/ml) was added sufficient 65% strength nitric acid to reach pH 2.7 (see Table 1). After 115 minutes, the mixture was cooled to 0° C. by ice, the sediment which had precipitated out was centrifuged off, rinsed with 100 ml of distilled $H_2O$ and centrifuged dry for 10 minutes. 312 g of solid having a moisture content of 22.9% were obtained. This is equivalent to 225.2 g (i.e. 93.9%) of anhydrous L-aspartic acid.

In addition, 123.7 g (124 ml) of wash water and 834.5 g (800 ml) of precipitation filtrate (mother liquor M1) were obtained. The wash water and M1 were adjusted to pH 9 using 25% strength ammonia water and then subjected to a nanofiltration. The roughly 20% ammonium nitrate solution thus obtained was concentrated to 65%. The distillate was added back to the crystallization process in later batches in step c).

TABLE 1

| Time min | g $HNO_3$ | ml $HNO_3$ | pH | Temp. |
|---|---|---|---|---|
| 0 | 0 | 0 | 10.2 | 23.4 |
| 10 | 71 | 49 | 9.0 | 30.5 |
| 20 | 88 | 63 | 8.0 | 29.8 |
| 25 | 95 | 65 | 6.0 | 30.0 |
| 35 | 117 | 84 | 5.0 | 30.1 |
| 40 | 135 | 98 | 4.5 to 5.4 | 30.1 to 31.3 |
| 55 | 150 | 108 | 5.4 | 30.6 |
| 65 | 186 | 133 | 5.0 | 32.6 |
| 90 | 229 | 166 | 4.5 | 32.2 |
| 100 | 247 | 178 | 4.0 | 32.5 |
| 105 | 255 | 184 | 3.5 | 32.4 |
| 110 | 259 | 186 | 3.0 | 32.2 |
| 115 | 262 | 190 | 2.7 | 31.6 |

What is claimed is:

1. A process for preparing L-aspartic acid by enzyme-catalyzed reaction of fumaric acid with ammonia, which comprises a) reacting fumaric acid with ammonia to form ammonium L-aspartate in the presence of aspartase or aspartase-producing microorganisms in an inert diluent, b) removing any excess ammonia from the reaction mixture and c) precipitating L-aspartic acid by adding nitric acid, separating it off from the reaction mixture, washing and drying it, then d) separating off residual L-aspartic acid and residual fumaric acid from the precipitation filtrate by nanofiltration, recycling the retentate to step c) and e) concentrating the filtrate from step d), adding the resultant distillate in step a) to any ammonia excess separated off in step b) and feeding the concentrated filtrate to a nitrogen fertilizer process.

2. The process as claimed in claim 1, wherein the diluent used in step a) is water, water/ethanol or water/acetone mixtures.

3. The process as claimed in claim 1, wherein step a) is carried out at a pH between 7 and 9.

4. The process as claimed in claim 1, wherein, in step b), a distillation is carried out at temperatures between 30 and 110° C. and at atmospheric pressure or under reduced pressure to remove said excess ammonia.

5. The process as claimed in claim 1, wherein step c) is carried out at a pH between 2 and 5.

6. The process as claimed in claim 1, wherein step c) is carried out at a temperature between 15 and 60° C.

7. The process as claimed in claim 1, wherein the nanofiltration in step d) is carried out at a pH between 4 and 11, at a pressure between 1 and 50 bar and at a temperature between 10 and 50° C.

8. The process as claimed in claim 7, wherein the pH is between 7 and 10.

9. The process as claimed in claim 1, wherein the filtrate from step d) is concentrated to an above 50 to 80% strength solution.

* * * * *